(12) United States Patent
Maillet et al.

(10) Patent No.: US 12,042,928 B2
(45) Date of Patent: Jul. 23, 2024

(54) ROBOTIC CONTROLS FOR A SURGICAL ROBOT

(71) Applicant: MedTech S.A., Montpellier (FR)

(72) Inventors: Pierre Maillet, Saint Aunes (FR); Florian Coiseur, Lattes (FR); Maxence François, Montpellier (FR)

(73) Assignee: MedTech S.A., Montpellier (FR)

( * ) Notice: Subject to any disclaimer, the term of this patent is extended or adjusted under 35 U.S.C. 154(b) by 946 days.

(21) Appl. No.: 16/985,697

(22) Filed: Aug. 5, 2020

(65) Prior Publication Data
US 2021/0039262 A1 Feb. 11, 2021

Related U.S. Application Data

(60) Provisional application No. 62/884,904, filed on Aug. 9, 2019.

(51) Int. Cl.
| | |
|---|---|
| B25J 13/04 | (2006.01) |
| A61B 34/00 | (2016.01) |
| A61B 34/20 | (2016.01) |
| A61B 34/30 | (2016.01) |
| B25J 13/08 | (2006.01) |

(52) U.S. Cl.
CPC ............... *B25J 13/04* (2013.01); *A61B 34/20* (2016.02); *A61B 34/25* (2016.02); *A61B 34/30* (2016.02); *A61B 34/70* (2016.02); *B25J 13/085* (2013.01); *A61B 2034/2074* (2016.02)

(58) Field of Classification Search
CPC ......... B25J 13/04; B25J 13/085; A61B 34/20; A61B 34/25; A61B 34/30; A61B 34/70; A61B 2034/2074; A61B 2017/00115; A61B 2034/252; A61B 2034/302; A61B 2034/742; A61B 2034/744; A61B 2090/064
See application file for complete search history.

(56) References Cited

U.S. PATENT DOCUMENTS

| | | |
|---|---|---|
| 7,643,862 B2 | 1/2010 | Schoenefeld |
| 8,095,200 B2 | 1/2012 | Quaid, III |
| (Continued) | | |

FOREIGN PATENT DOCUMENTS

| | | |
|---|---|---|
| EP | 3431032 A1 | 1/2019 |
| WO | WO-2019023386 A2 | 1/2019 |

OTHER PUBLICATIONS

"European Application Serial No. 20189922.6, Extended European Search Report dated Dec. 18, 2020", 8 pgs.
(Continued)

*Primary Examiner* — Harry Y Oh
(74) *Attorney, Agent, or Firm* — SCHWEGMAN LUNDBERG & WOESSNER, P.A.

(57) ABSTRACT

Systems and methods may be used for registering a force input on a portion of a surgical robot, for example using a force sensor of the surgical robot. The force input may correspond to a control command. The control command may generate a change in a control mode of the surgical robot, validate a step of a workflow in planning or navigation software, or the like. A visual indication may be provided, for example using a light of the surgical robot. The visual indication may indicate that the control command has been identified or executed.

18 Claims, 15 Drawing Sheets

(56) References Cited

U.S. PATENT DOCUMENTS

| | | | |
|---|---|---|---|
| 2009/0041565 A1* | 2/2009 | Rodriguez Y Baena | ..................... A61B 34/70 414/431 |
| 2013/0184871 A1 | 7/2013 | Fudaba et al. | |
| 2016/0361125 A1 | 12/2016 | Balicki et al. | |
| 2017/0315536 A1* | 11/2017 | Brusky | ................ G05B 19/402 |
| 2018/0056504 A1* | 3/2018 | Ting | ..................... G05B 19/421 |
| 2018/0110573 A1 | 4/2018 | Kostrzewski | |
| 2018/0200002 A1* | 7/2018 | Kostrzewski | .......... G02C 7/049 |
| 2018/0263714 A1* | 9/2018 | Kostrzewski | ...... A61B 17/1703 |
| 2018/0289435 A1* | 10/2018 | Namiki | .............. A61B 17/0469 |
| 2018/0333213 A1 | 11/2018 | Johnson et al. | |
| 2019/0202066 A1 | 7/2019 | Maret | |
| 2019/0327394 A1* | 10/2019 | Ramirez Luna | ....... H04N 23/51 |
| 2020/0324408 A1* | 10/2020 | Bourlion | .............. A61B 5/4566 |

OTHER PUBLICATIONS

"European Application Serial No. 20189922.6, Response filed Aug. 10, 2021 to Extended European Search Report dated Dec. 18, 2020", 20 pgs.

* cited by examiner

ROBOTIC CONTROLS FOR A SURGICAL ROBOT

CLAIM OF PRIORITY

This application claims the benefit of priority to U.S. Provisional Application Nos. 62/884,904, filed Aug. 9, 2019, titled "ROBOTIC CONTROLS FOR A SURGICAL ROBOT"; which is hereby incorporated herein by reference in its entirety.

BACKGROUND

Surgeries are increasingly being performed with the aid of Computer Assisted Technologies (CAT), including Computer Assisted Surgery (CAS), Surgery with CAT includes several types of technologies, such as active robotics, passive robotics, optical or electromagnetic navigation systems, planning software, intraoperative imaging systems, among others. Those technologies are used to assist surgeons in order to perform more accurate, safer, faster and less invasive surgeries.

Currently, interactions between technologies and surgeons are performed by: remote controller hand held by surgeon, pointer probe hand held by surgeon, free hand gestures, a keyboard, a mouse, a touch screen, or a foot pedal. However, these solutions do not permit surgeons to stay focused on the surgical field and their patients as surgeons have to interact with external devices, which are not directly linked to the surgical field or patient. Additional drawbacks of these techniques are that surgeons have to check, on a display device which is generally outside the surgical area, if the action has actually occurred at the CAS system. Field of view may present issues as well, such as for the pointer probes or for free hand gestures which are linked to an optical navigation system/tracking camera. Other drawbacks of these techniques include electromagnetic disturbance issues, sounds disturbance issues, a limited number of possible interaction actions, such as for the foot pedal, or that these solutions are unintuitive, not user friendly, or inaccessible for a given procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
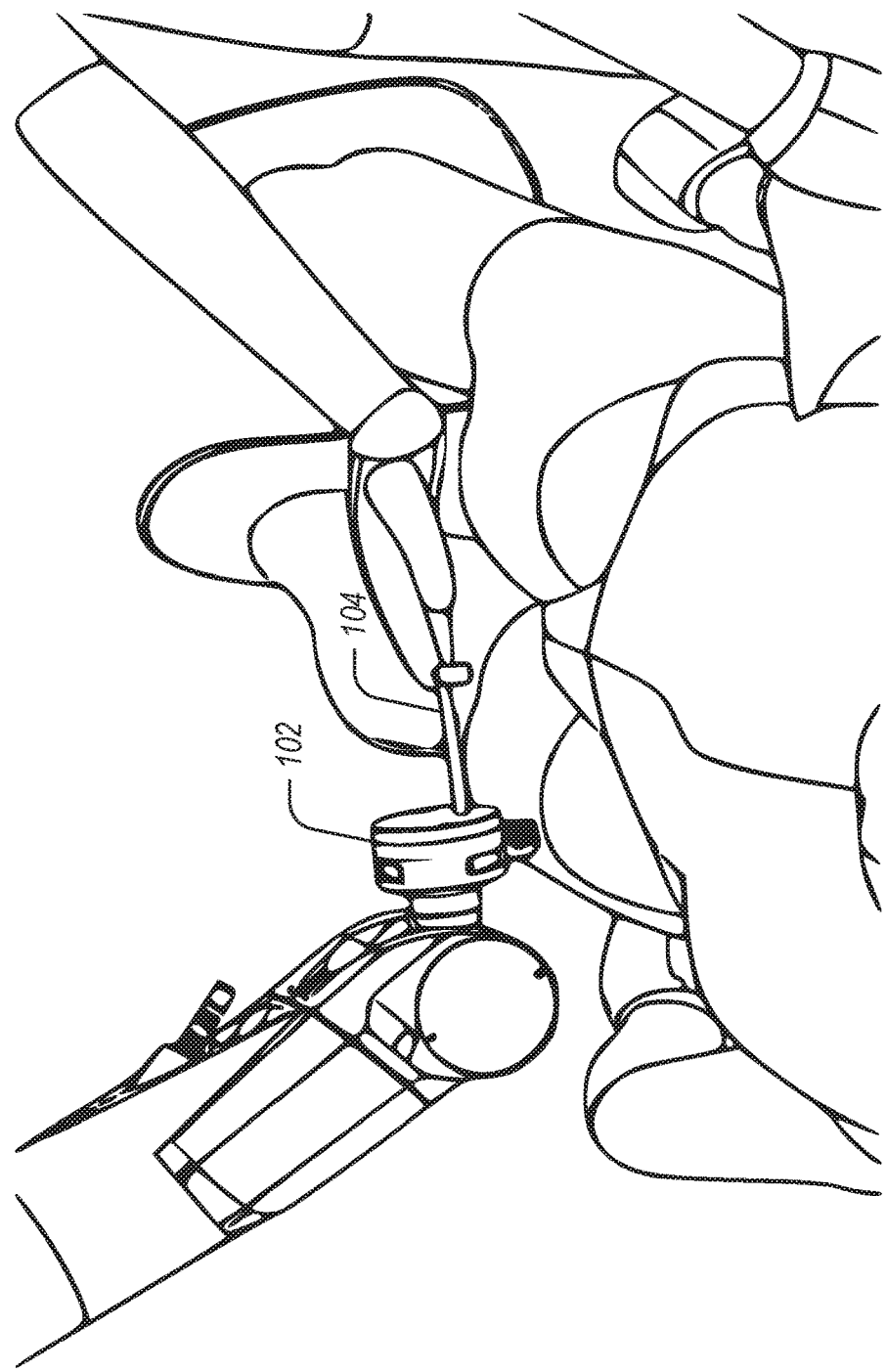
FIGS. 1A-1E illustrate surgical robot systems in accordance with at least one example of this disclosure.

Systems and methods for facilitating interaction between a surgeon and a surgical robot are described herein. These systems and methods allow for robotic or software controls during surgical applications. For example, moving a portion of a robot or applying a force to a portion of a robot may be used to control the robot or other aspect (e.g., a portion of a user interface) of a surgical system.

During surgeries using CAT, interactions between technology and a surgeon may be a key factor in effectiveness or fluidity of related surgical workflow or time saving during a procedure. For example, successful adoption of technology in the operating room may be contingent on comfort, ease, accessibility, or desire to use technology by the surgeon. Making interactions between technology and a surgeon easy or natural allows the surgeon to stay focused on a surgery and a patient. Technologies are best when they disturb the surgeon as little as possible. For example, disturbances may occur when the surgeon is overly interacting with technology, such as a touch screen, instead of focusing on the patient. This example may occur when validation of steps of a surgical workflow are required for a given technology (e.g., navigation or robotic systems).

The systems and methods described herein provide for improved interaction between technology and a surgeon by presenting a solution that is easier, more comfortable (e.g., natural), and accessible than existing techniques. The systems and methods described herein permit a surgeon to stay focused on a surgical procedure and a patient as much as possible, while avoiding disturbances, being intuitive and user friendly, and improving the effectiveness of a surgical workflow.

In general, the systems and methods discussed herein allow a surgeon to interact with portions of a CAS system through data received from sensors embedded within devices controlled by the CAS system or data received from the surgeon's interaction with the devices (e.g., a robotic arm). In an example, a robotic arm may include a force sensor configured to detect pressure applied by a surgeon. The system may interpret certain patterns of input directed at the senor as control inputs, and filter other signals from the force sensor as relating to standard operation of the robotic arm or device or as a result of inadvertent contact with the robotic arm or device. The inputs may then be mapped to desired functions, such as a change of robot control mode or validation of a workflow step of a planned surgery. For example, in a neurosurgery where the surgical plan includes the insertion of instruments or implants at several planned trajectories into the brain or spine, the CAS system may receive a control input to switch to the next planned trajectory when the surgical work on the previous trajectory is complete.

The systems and methods described herein may be used to improve or control interactions between a surgical robotic device, navigation or planning software associated with the surgical robotic device or CAS system, and a surgeon.

FIGS. 1A-1E illustrate surgical robot systems in accordance with at least one example of this disclosure.

FIG. 1A shows a detailed view of a surgeon interaction with a robotic arm. The interaction includes a tap or continued pressure applied by a surgeon on an instrument mounted on an end effector of the robotic arm.

Figure 1B:
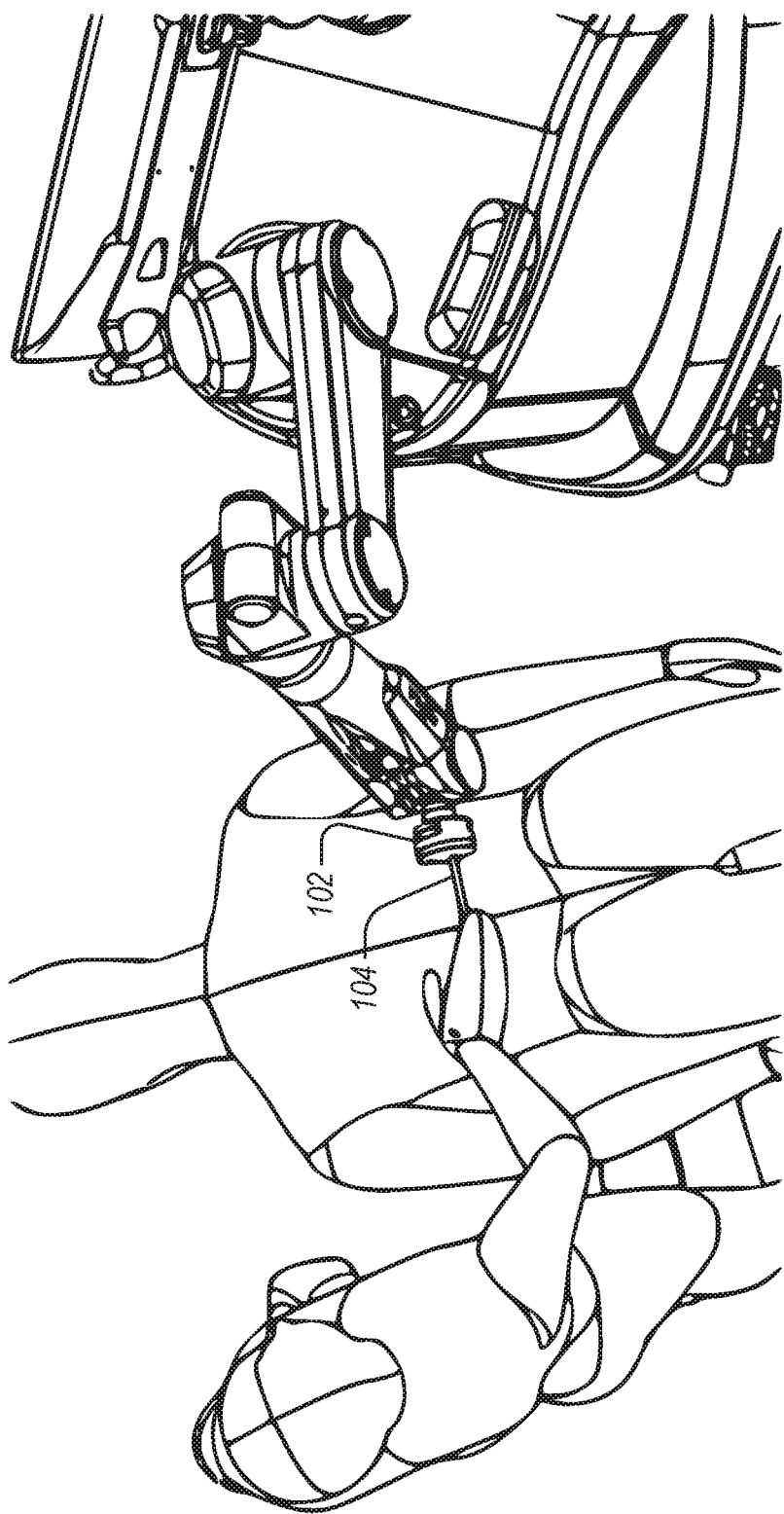

FIG. 1B shows a top view of a tap or continued pressure applied by the surgeon on the instrument mounted on the end effector of the robotic arm.

Figure 1C:
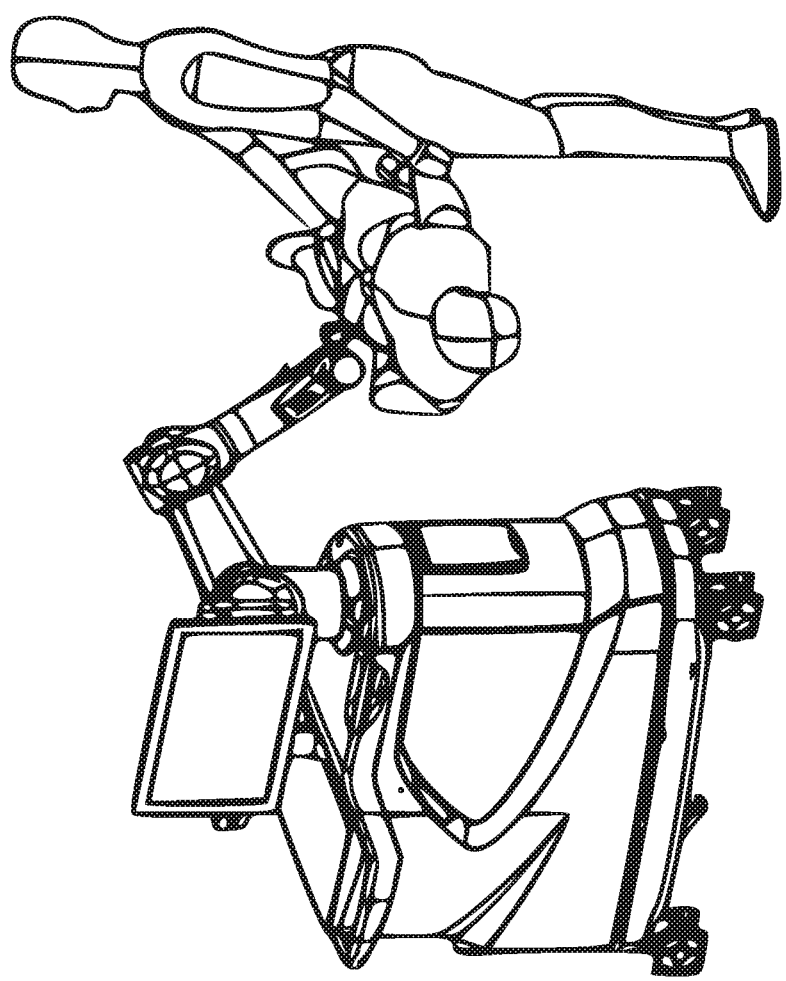

FIG. 1C shows a global view of a tap or continued pressure applied by the surgeon on the instrument mounted on the end effector of the robotic arm.

Figure 1D:
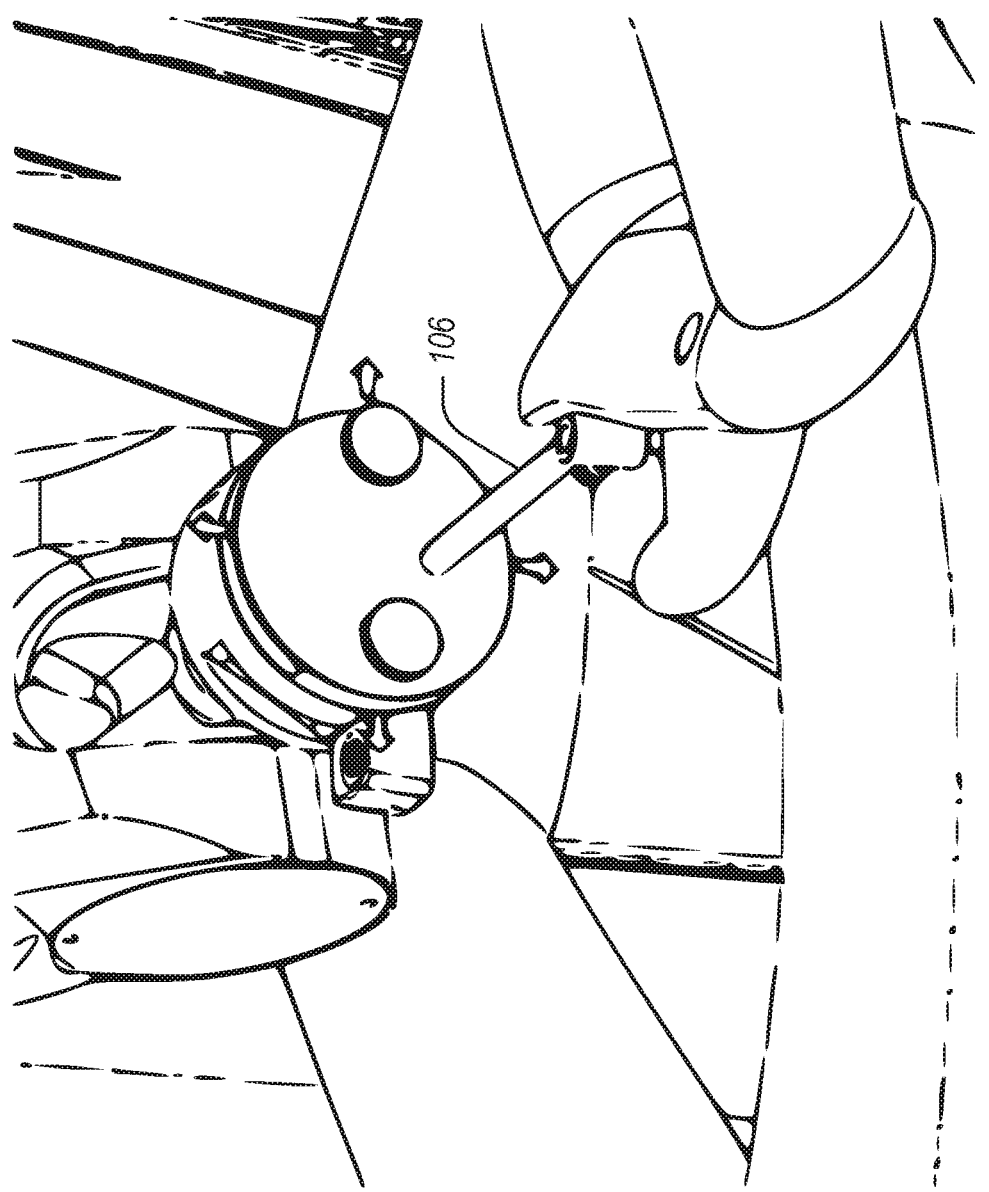

FIG. 1D shows an illustration of directions of movement of a force sensor of the end effector of the robotic arm. In an example, the force sensor may be used as a joystick 106 (e.g., with 6 degrees-of-freedom (DOF)), such as for use as a virtual mouse (e.g., to control a user interface component, to control the robotic arm, or the like).

Figure 1E:
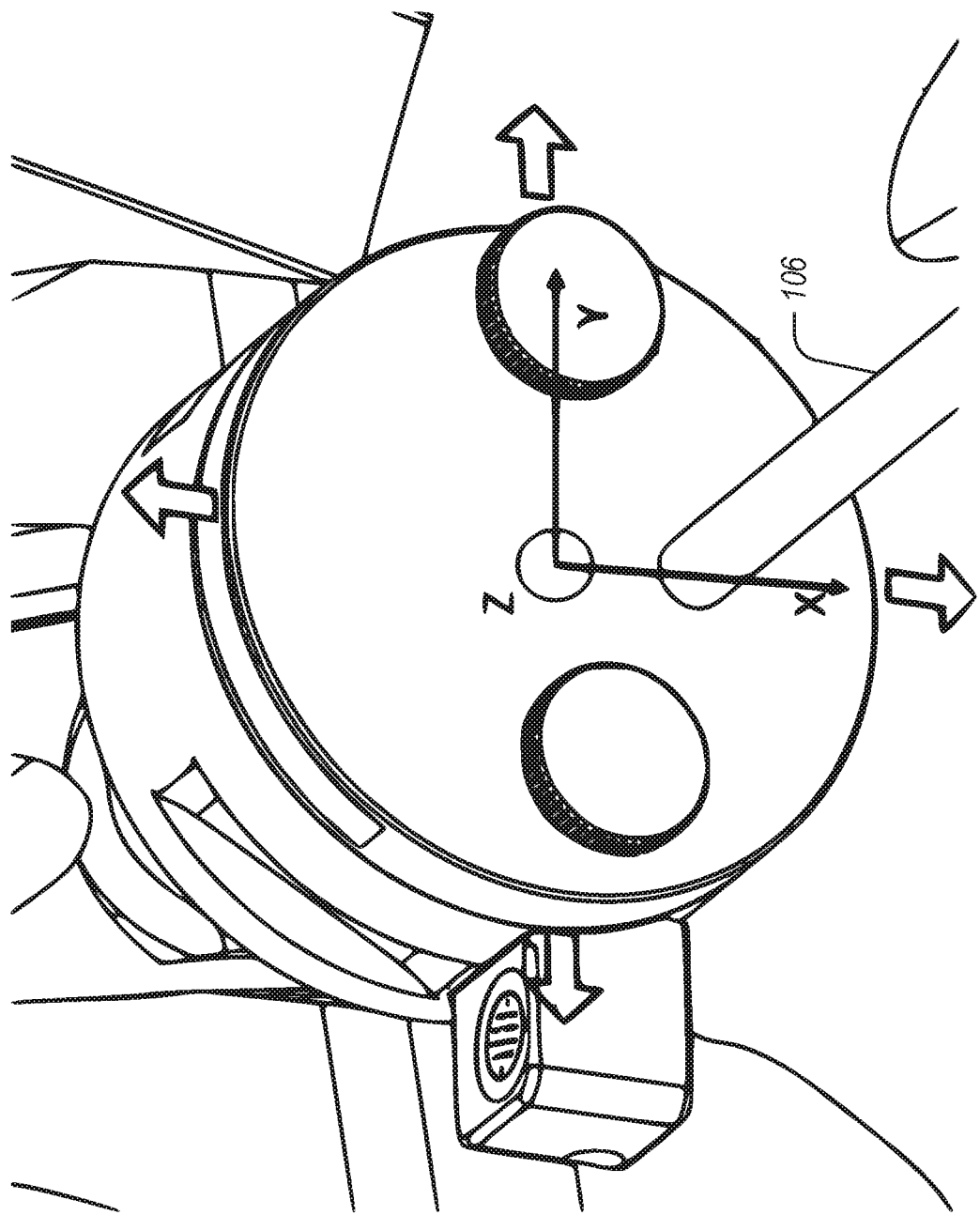

FIG. 1E shows an example reference frame of the force sensor. In this example reference frame, the x-y plane is perpendicular to an instrument extending from the robotic arm, or parallel to the face of the end effector or force sensor. The z-axis is aligned along the major axis connecting the instrument to the robotic arm.

When using a surgical robotic system or a navigation system interactions occur between a surgeon or other user and the robotic or navigation system. The interactions may include entering control inputs to the robotic system, the navigation system, software, or a user interface. Such control inputs may be of various kinds, for example activating a certain robotic control mode (e.g., automatic, cooperative, constrained modes, such as axial, isocentric or planar, or the like) or moving forward or backward one or more steps in a sequence of steps in a planned surgery (e.g., calibration, registration, pre-operative evaluation, resections, trialing, implantation, post-operative evaluation, etc.), or the like.

Typical interaction techniques between a user (e.g., a surgeon) and a surgical robotic system or navigation or planning software may include for example using a pointer probe, a free hand gesture, audio signals (including voice commands), a keyboard, a mouse, a touch screen, or a foot pedal. The systems and methods described herein use a force input on a robotic arm, and the force input may be used to replace any or all of the typical interaction techniques.

In an example, a force sensor 102 shown in FIG. 1A may include a sensor or a combination of sensors. The force sensor 102 may have a tool 104 affixed to a distal end of the force sensor 102. The force sensor 102 and the tool 104 may be located at a distal end of a robotic arm. A robotic system may include a robotic arm, a robotic mobile stand, or other robotic device. A force input to the robotic system may be used to detect an interaction with the robotic system, which may be used to generate a change of robot control mode, validate a workflow step of a planned surgery, or modify a component of a user interface. For example, a force input may cause switching to a next planned trajectory when the surgical work on a previous trajectory is completed. In a specific example, in a typical robotically assisted spinal surgery, the surgeon may pre-operatively or intraoperatively plan placement (location and trajectory) of multiple pedicle screws used to facilitate spinal fusion. During the actual robotic procedure, once a first screw insertion is completed, the input mechanism discussed here may be used by the surgeon (without taking attention away from surgical field) to indicate that the robot should reposition for the next pedicle screw. In another example, a robot may be used to follow planned trajectories in brain surgeries involving electrodes the placement of electrodes in the brain. In yet another example, the input mechanism discussed here may be used in robotically-assisted knee surgeries, such as to switch from tibial cut planes to femoral cut planes.

In an example, when a surgeon wants to change a control mode of the robotic arm (or provide a similar input), the surgeon may apply a tap (e.g., a tap force input), or push or pull in a specific direction or amplitude and apply a sustained force input, such as directional force input, which may occur for a certain time (e.g., a different command may correspond to a sustained force input over 1 second, 2 s, 3 s, etc., depending on the command the surgeon would like to execute). In another example, the robotic arm may detect forces or torques input over a period of time or only during a certain time period. For example, for 2 seconds after a surgeon presses a foot pedal, a force input on the robotic arm may be detected as an input command. In another example, the robotic arm may interpret a force input as an input command during specific time periods, such as between procedure steps, after a portion of a procedure is completed, when no procedure portion is active, etc. Another example input may include a combination of several signals in the same time, for example, the surgeon may only interact with the robot when the vigilance device (e.g., foot pedal) is released.

The force input may be applied by the surgeon on an instrument held by the robotic arm (e.g., as shown in FIGS. 1A-1E). In another example, a force input may be used to switch a control mode of the robotic arm (e.g., from automatic mode to cooperative mode or axial constrained mode, stopping an automatic movement, changing the speed of the robot, such as from a fast cooperative mode to a slow one, or the like). The tap or grab applied to the instrument may generate a specific electrical signal (e.g., voltage) which may be detected by using data provided by a force sensor, by data provided by the motors on the joints of the robotic arm, or by analyzing the electrical current signal and or torques of said motors. The force input signal may be compared (e.g., using a processor) with a preregistered reference signal, such as a signal stored on a database. In an example, a preregistered reference signal may be linked, in the database, to a command for the CAS system (e.g., a control command for the surgical robot or a control command for navigation or planning software), When there is a match between the signal generated by the surgeon and a preregistered reference signal stored in the database, the processor may cause the command corresponding to the preregistered reference signal to be implemented (e.g., cause the action to be taken by the surgical robot or the navigation or planning software), The signal may be configured with surgeon preferences by registering the surgeon's interaction when delivering the device and storing such registration in a database.

In another example, the surgeon may be notified that the command has been recognized by the system. After conveying the notification to the surgeon, the CAS system (in one example, the robotic or navigation device) may perform the command associated with the preregistered reference signal. In this example, the surgeon may confirm or deny the action before it is performed or completed. For example, the surgeon may be notified using audio or a visual indicator (e.g., light, a symbol, etc.), and a confirmation may be requested to perform an action, such as by using the audio to ask the surgeon to apply a tap or sustained force input on the robotic arm or a light blinking to confirm the action.

A database of preregistered signals may be configured using a surgeon or user preference of use, in an example. Predefined actions or interactions performed by the surgeon on the instrument held by the robotic arm may generate a command for the CAS system depending on a particular surgical procedure being performed or the surgeon's preferences. The signals may be configured with surgeon preferences by registering surgeon's interaction when delivering the device and storing the registrations between interactions and preferences in a database.

In order to avoid disturbances relative to checking whether the intended action has been identified by the CAS system, a light or sound device may be used. For example, the end effector of the robotic arm may include a light or the robotic system may include a speaker. When the action is recognized by the system the light or sound device may emit a particular light color or sound to confirm to the surgeon that the action has been taken into account. In an example, a particular light or color or sound may correspond to not recognizing the action. For example, when the intended action is recognized by the system, a lighting device may emit a blue or green light. Those colors generally correspond to permission, but other colors may be used. In an example, when the intended action is not recognized by the system, a lighting device may emit a red or yellow color. Those colors generally correspond to prohibition or caution, but other colors may be used. When the intended action is recognized by the system, a sound device may emit a high or low pitched sound which may be quick or long. The sound output may be configured depending on a surgeon's preferences. In another example, speech audio may be output (e.g., "action X recognized"). When the intended action is not recognized by the system, a sound device may emit a high or low pitched sound, which may be quick or long. The sound output may be configured depending on a surgeon's preferences. In another example, speech audio may be output (e.g., "action not recognized").

This way of conveying to the surgeon whether the intended action has been recognized avoids requiring the surgeon to look at a user interface, or otherwise change where the surgeon looks. For example, this technique may avoid disturbing the surgeon during the surgical procedure by requiring checking, on a display device, which is generally located outside the surgical area, whether the intended action has been recognized.

In an example, the surgeon may use an instrument held by a robotic arm as a 6 DOF (x,y,z,r (roll),p (pitch),y (yaw)) joystick 106 (or a kind of 6 DOF virtual mouse) to remotely control a cursor of a computer system (e.g., as shown in FIGS. 1D-1E). The force applied by the surgeon on the instrument may generate a signal, which may be detected using the data provided by force sensor or by data provided by the robotic arm joints motors. This signal may be used as a command in order to move the cursor, presented on a user interface of a display screen. Force input at the instrument may result in corresponding movement of the cursor in the same direction as the force applied, and optionally at a corresponding speed, for example based on amplitude or variation of amplitude of the force applied. For example, the amplitude, orientation, or direction of the applied force may be used to determine the movement amplitude, orientation, direction, or speed of the cursor on the screen. Other actions may be taken such as right, left, simple, or double click (e.g., as would be done using a mouse) may be implemented by defining an interaction, such as a tap or a quick or long push or pull on the instrument for simple click, double tap for double click, or the like. In an example, a sequence of actions performed by surgeon may be define as an action to be realized by the CAS system.

In another example, instead of using only data from one sensor a combination of data provided by different sensors (such as force sensor data and foot pedal data or force sensor data and laser rangefinder data, etc. may be used. The sensors may be embedded on or attached to the surgical robotic device (e.g., on a robotic arm or a robotic mobile stand), and used to detect a surgeon interaction with the robotic system. The input may cause a change of robot control mode or validate a workflow step of a planned surgery. For example, the input may cause a change to a next planned trajectory when the surgical work on previous trajectory is complete. Using a combination of sensors may allow for redundant information for safety purposes or for increasing the number of possible identifiable interactions.

Figure 7:
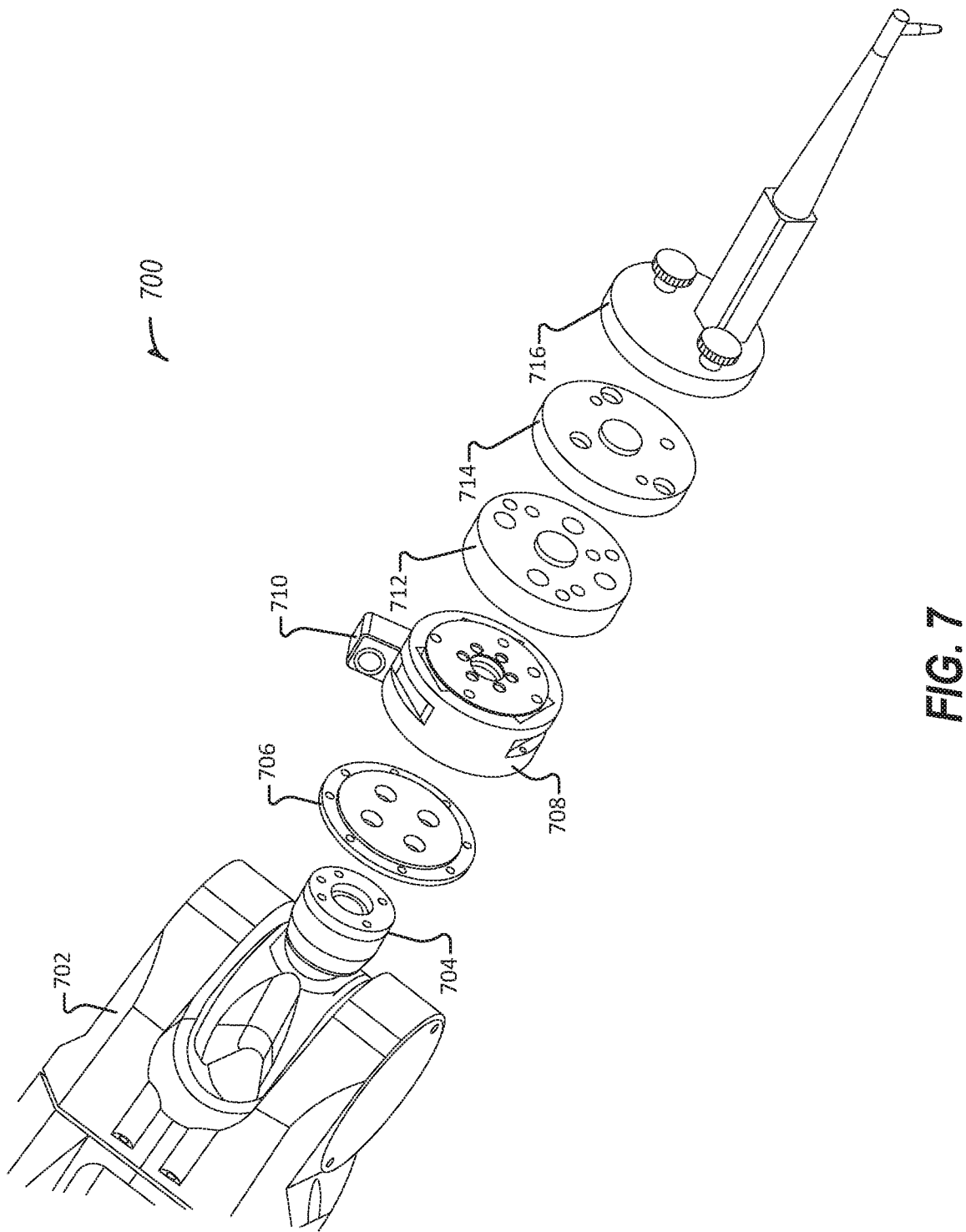
FIG. 7 illustrates an exploded view of a surgical robotic device in accordance with at least one example of this disclosure.

The surgical robotic device may include a ROSA® robotic device (manufactured by Zimmer CAS of Montreal, Quebec CA), for example the ROSA® Knee System. Surgical robotic devices such as the ROSA® Knee System include a robotic arm configured to include an end effector, which may include a force sensor or have a force sensor coupled to the end effector. A removable tool may be affixed to the end effector, which may be used as an input device to apply a force to the arm portion of the surgical robotic device. An example surgical robotic device is shown in FIG. 7 below. In an example, the robotic arm may be extended over a surgical table, such that it may be used in a surgical procedure or controlled by a surgeon as an input device. For example, the robotic arm may be no more than half the operating table away (e.g., centered over the table, extended from an opposite side of the table, or the like).

Figure 2A:
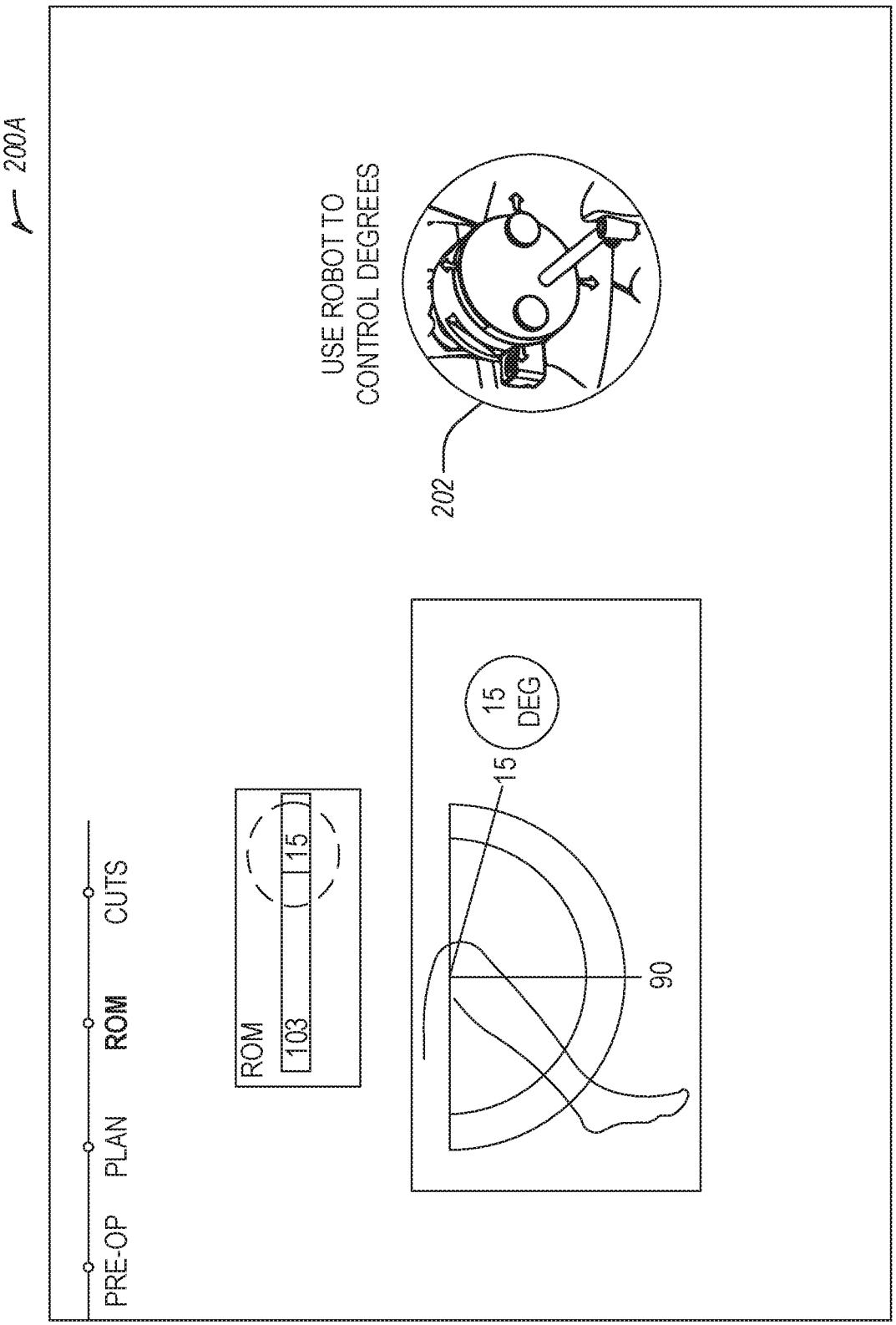
FIGS. 2A-2C illustrate a user interface for use with the surgical robot systems described herein in accordance with at least one example of this disclosure.
Figure 2B:
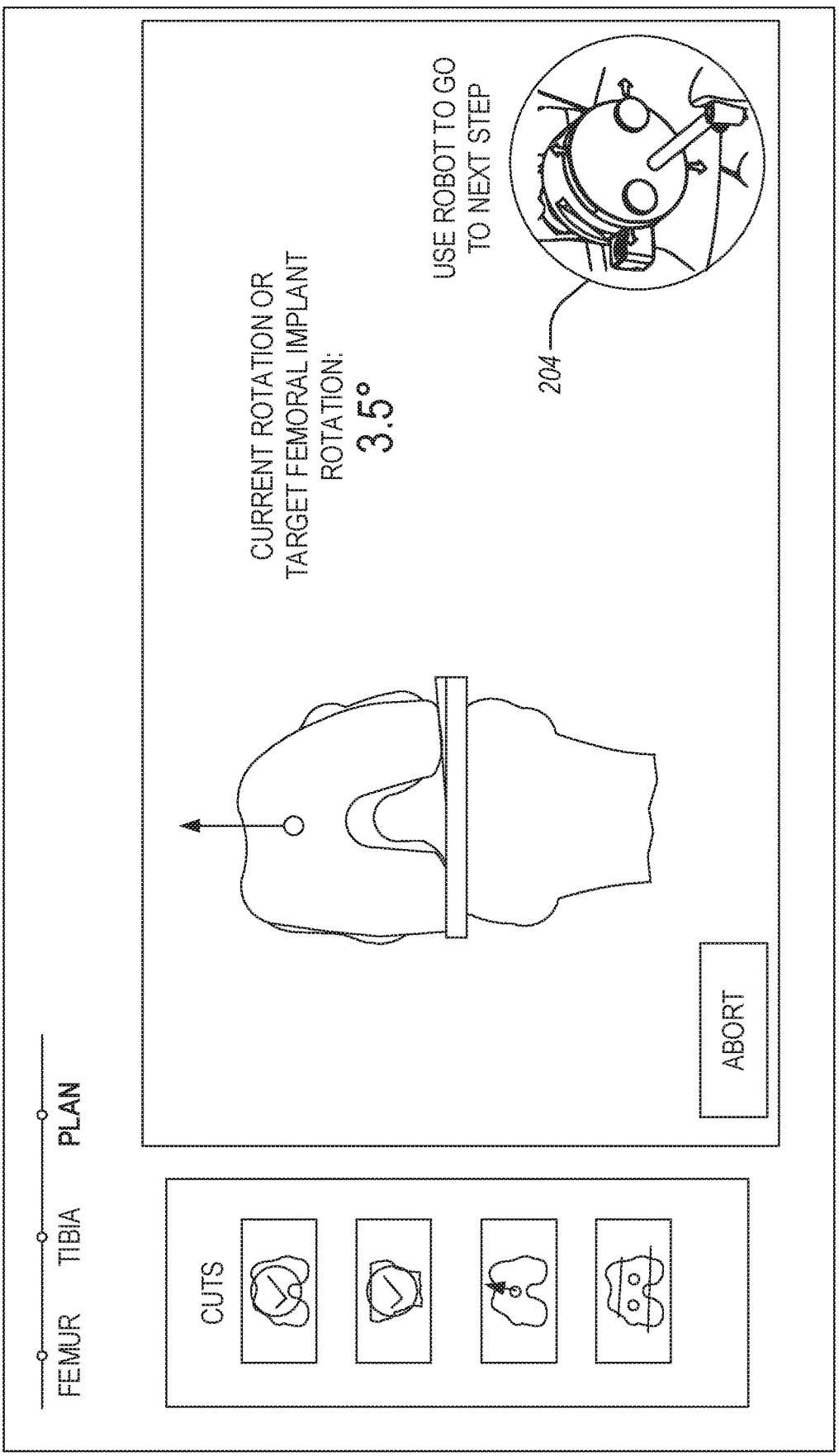
Figure 2C:
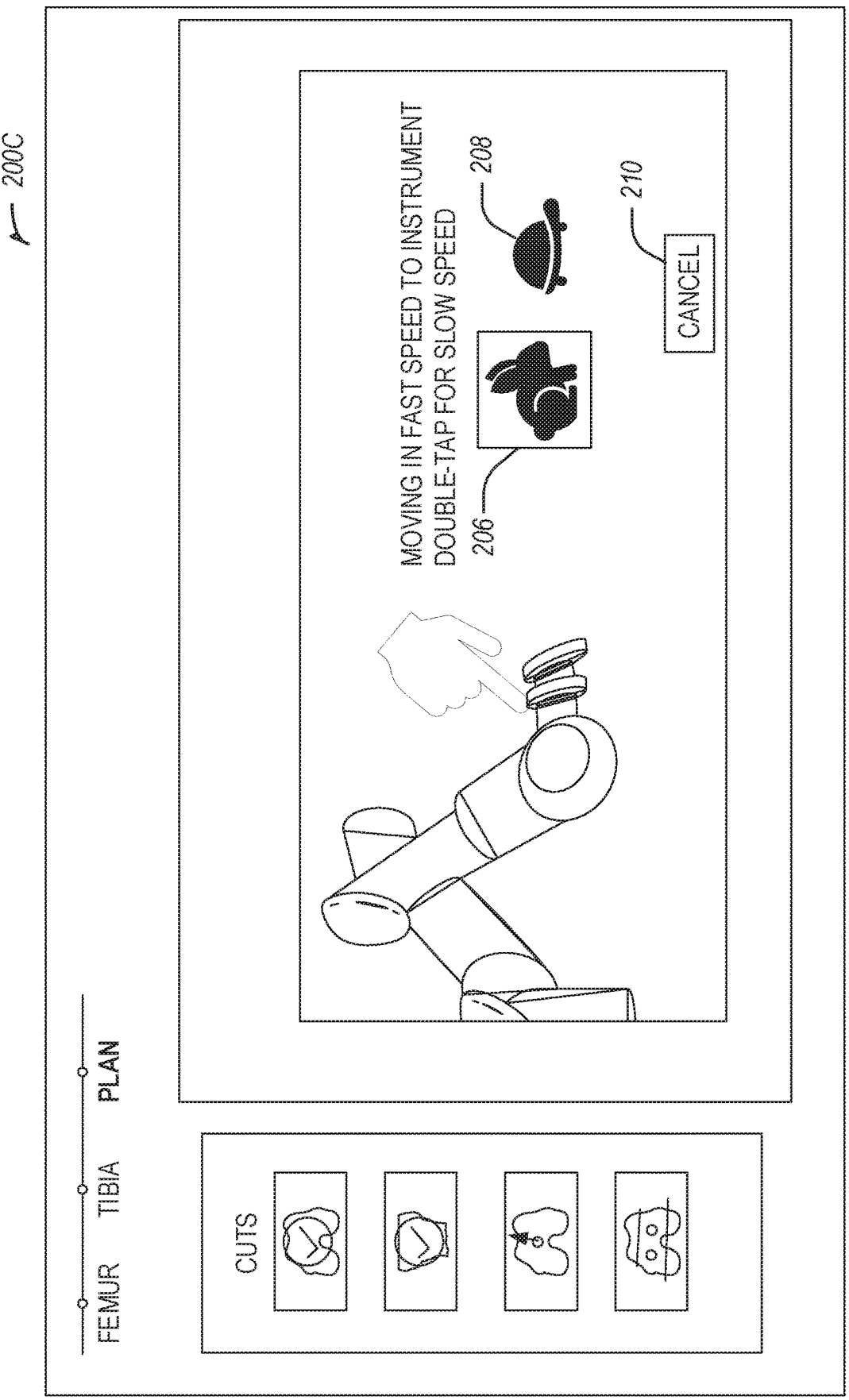

FIGS. 2A-2C illustrate user interfaces 200A-200C for use with the surgical robot systems described herein in accordance with at least one example of this disclosure. The user interfaces 200A-200C are shown as an example; other user interface components or user interfaces for other procedures may be used with the systems and methods described herein. Further, the user interfaces 200A-200B illustrate an example for changing a component of a user interface (in user interface 200A) and an example for changing to a new user interface or component or to generate a new user interface or component (user interface 200B). User interface 200C illustrates a speed control feature for movement of a robotic arm. Other controls may be implemented with the systems and methods described herein, such as controlling a device (e.g., the robotic arm itself, a light, a table height, other surgical devices such as a saw, or the like) or other computer components, such as a networking device, a phone, a remote computing device, etc.

The user interface 200A includes a control indication 202 that may be used to adjust aspects of the user interface 200A. For example, a range of motion may be shown that may be rotated through different positions (e.g., to different degrees). The control indication 202 may adjust the position of a user interface component or control an aspect of the component of the user interface. The control indication 202 itself may be controlled by a force input on a robotic arm.

In an example, a force input on a robotic arm may be used to control a cursor on the user interface 200A. In an example, a first force input may be used to select a component, such as the control indication 202 of the user interface 200A, and a second force input may be used to change an aspect of the user interface 200A. The first or second force input may be a tap, a sustained input, a gesture, etc. In an example, a tap may initiate control of the control indication 202 followed by a gesture to control the aspect of the user interface 200A controlled by the control indication 202. In an example, a gesture may include a sustained force input for longer than a tap, where a tap may be a few milliseconds of force input and a sustained force input may be anything longer than a few milliseconds.

The user interface 200B includes a control indication 204 that may be used to change at least a portion of the user interface 200B. For example, the control indication 204 may cause the user interface 200B to change to a next step in a surgical procedure, which may include generating a new component, removing a component, generating a new user interface, or the like. Changes caused by the control indication 204 may result in changes to a robotic arm. In an example, when the robotic arm receives a force input to result in a change to a next step in a surgical procedure, the robotic arm may move automatically based on a planned position for the next step. The robotic arm may take other actions in response to initiation of the next step, such as changing modes (e.g., from autonomous to collaborative or vice versa increase or decrease resistance or force assistance, or the like.

Actions taken using a robotic arm as a controller may result in changes to the user interfaces 200A-200B without other interaction on the user interfaces 200A-200B. For example, when a force input is received, a component of a user interface may change without any input directly on the user interface. Thus, while the user interface may change throughout a procedure, a surgeon may not need to actually interact with the user interface. Instead, the surgeon may look at it when convenient, or other people in the procedure room may view or interact with the user interface.

In an example, control of the user interfaces 200A-200B using a force input on a robotic arm may be combined with use of a foot pedal. In an example, when a foot pedal is depressed, the robotic arm may activate collaborative movement, or when pedal is not depressed, the robotic arm may respond to control commands (or collaborative movement may occur when foot pedal is not depressed, while control commands occur when depressed). In another example, a foot pedal may control whether force input on the robotic arm is used for controlling a cursor on a user interface or to interact with a component of the user interface. For example, activating or deactivating a foot pedal may cause a cursor mode where a cursor is moved around a user interface in response to the force input, while doing the opposite with the foot pedal causes a component to change (e.g., change values). In an example both uses of a foot pedal may be combined, such as by using a two-input foot pedal, two foot pedals, or taps or holds on the foot pedal. For example, tapping once may activate a collaborative mode, tapping twice may activate a cursor mode, and holding the foot pedal down may activate an interaction mode where a component of the user interface is modified. Other combinations of foot pedal, force input, and control action may be used with the systems and methods described herein.

The user interface 200C includes options for controlling speed of a robotic arm, for example when moving within a surgical field. The movement may include a plurality of speeds, such as over a range, or a binary choice of speeds, such as a fast speed option illustrated as selected on the user interface 200C by user interface indicator 206 and a slow speed option illustrated as not selected by user interface indicator 208. A cancel movement icon 210 may be selectable to stop the robotic arm from moving, in an example. The speed controls may be used for a particular movement of the robotic arm, such as movement to an instrument, to a patient, within a free drive area, within an interactive area, or the like. The speed controls may be selected using a double tap on the robotic arm. For example, tapping the robotic arm twice within a time period (e.g., half a second) may toggle speed between fast and slow. In another example, tapping the robotic arm twice within a time period may toggle among fast, slow, and stopped (e.g., cancel movement). The user interface 200C may provide instructions for the double tap, in an example. In some examples, confirmation on the user interface or via the robotic arm (e.g., with audio feedback) may be used to confirm a change in speed.

In an example, a robotic arm may quick connect to an instrument. A quick connect may include any connection that occurs in a short amount of time, such as a few milliseconds, a second, a few seconds, etc. A quick connect may include any connection that operates using a single action, such as a magnetic connection, a snap connection, a latch, a twist connection, or the like. In an example, the robotic arm may connect to an instrument using a quick connection when the instrument is placed first, and then the robotic arm is connected. For example, an instrument may be placed for a surgical procedure, and then the robotic arm may be brought to the instrument (e.g., automatically, using a force assist, etc.) and connected. In an example, the instrument may be placed and the robotic arm may be controlled to move faster or slower based on an interaction, such as a double tap on the robotic arm as described above and optionally shown in user interface 200C. For example, the robotic arm may be moved quickly toward the instrument, slowed when close to the instrument, and then connected to the instrument using a quick connect. This speed change functionality may be used, by way of example, in a hip arthroplasty surgery to facilitate the connection of the robotic arm to instruments, such as an impactor or reamer, that have a distal end in position in the surgical incision. The user may move the robotic arm at high speed to the general vicinity of the connection interface of the surgical tool (such as a quick connect protruding from a housing encapsulating the instrument). Once the robotic arm is in the general vicinity of the surgical instrument, the user may double tap the robotic arm to toggle the speed to a slower speed to facilitate connection (i.e. docking) a connection interface of the robotic arm to the corresponding connection interface of the instrument.

Figure 3A:
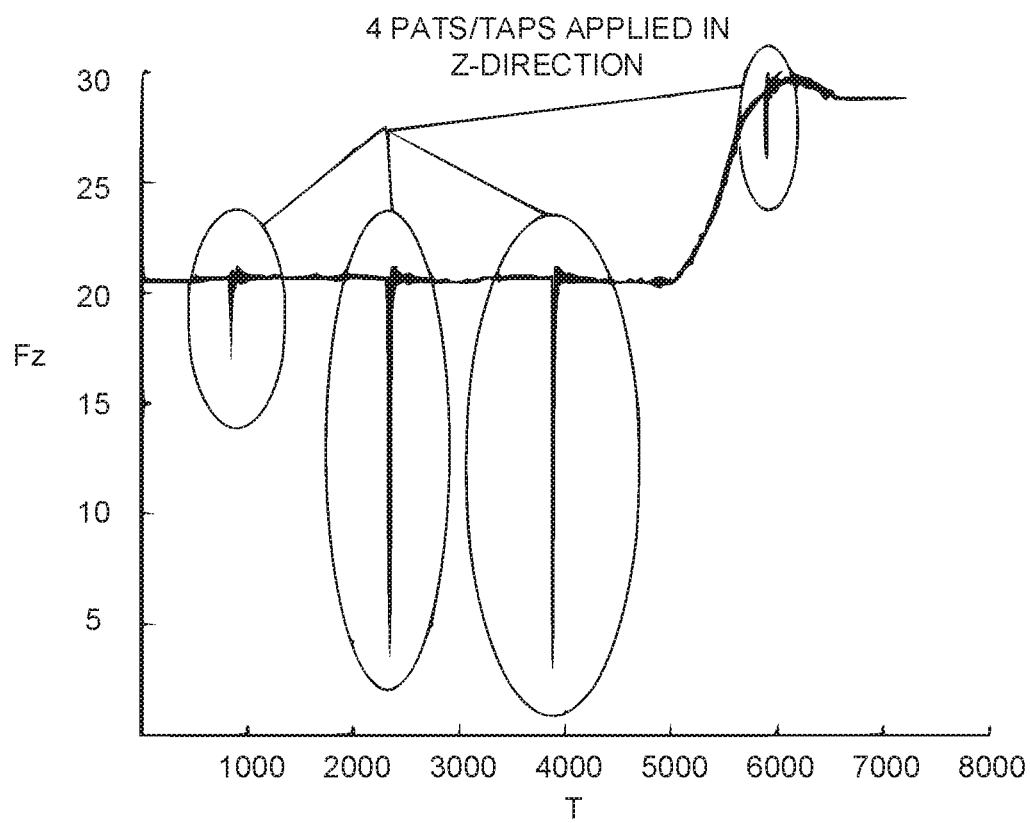
FIGS. 3A-3F illustrate force sensor input data over time in accordance with at least one example of this disclosure.
Figure 3B:
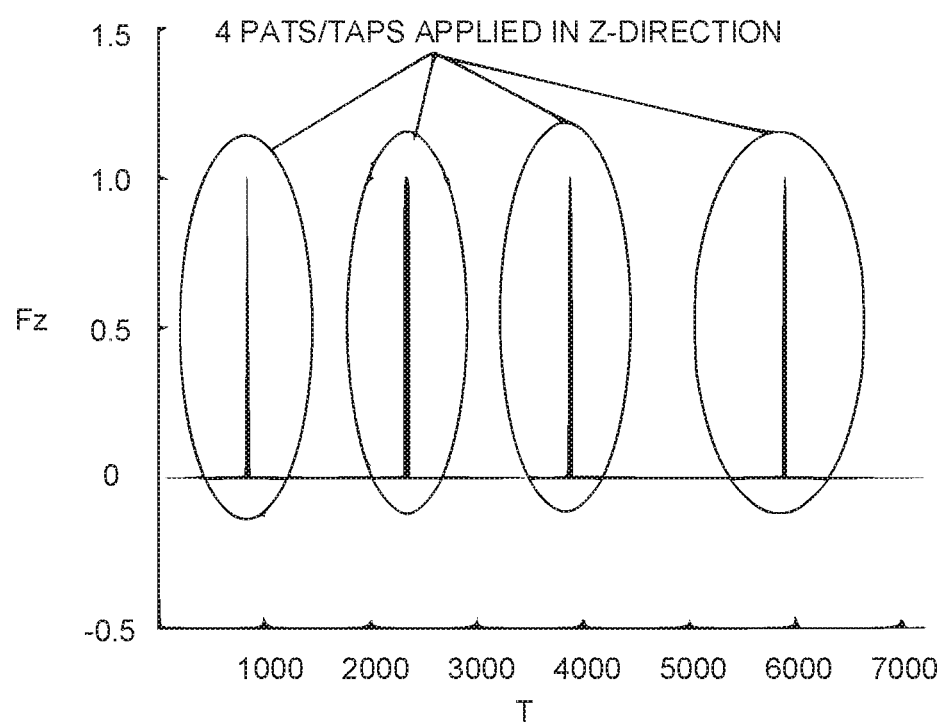

FIGS. 3A-3F illustrate force sensor input data over time in accordance with at least one example of this disclosure. In an example, FIGS. 3A-3B show detection of a tap applied on a robotic arm in a Z-direction using a force sensor of the robotic arm.

In an example, a control mode of the robotic arm may be changed by applying a tap (e.g., a tap force input), or grab with a sustained force input, such as directional force input, which may occur for a certain time (e.g., a different command may correspond to a sustained force input over 1 second, 2 s, 3 s, etc., depending on the command the surgeon would like to execute). The tap force input is shown in FIGS. 3A-3B, including multiple taps applied in FIG. 3A (four shown, the first and last with low intensity, and the middle two with high intensity) and in FIG. 3B (four shown). In another example, a force input may be used to switch a control mode of the robotic arm (e.g., from automatic mode to cooperative mode or axial constrained mode or the like). The tap or grab applied to the instrument may be compared (e.g., using a processor) with a preregistered reference force value (e.g., a threshold). When the tap or grab traverses the threshold, an input may be registered. For example, in FIG. 3A, a tap threshold may be set at "10" such that when the tap force goes below 10, a threshold has been traversed and a tap is registered. Similarly, in FIG. 3B, a tap threshold may be set at "0.5" such that when the tap force goes above 0.5 a tap is registered. In a grab situation, the threshold may include a temporal component such that the force value must be traversed for a minimum amount of time before the grab is registered or the grab may correspond to a traversal of a threshold for a specific amount of time.

Figure 3C:
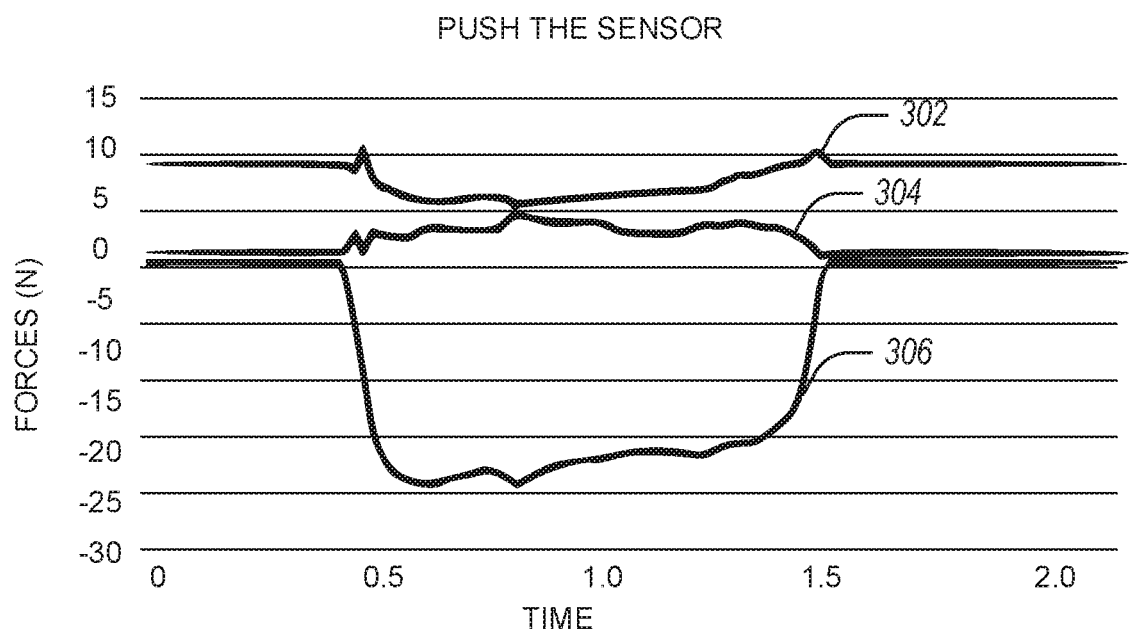
Figure 3D:
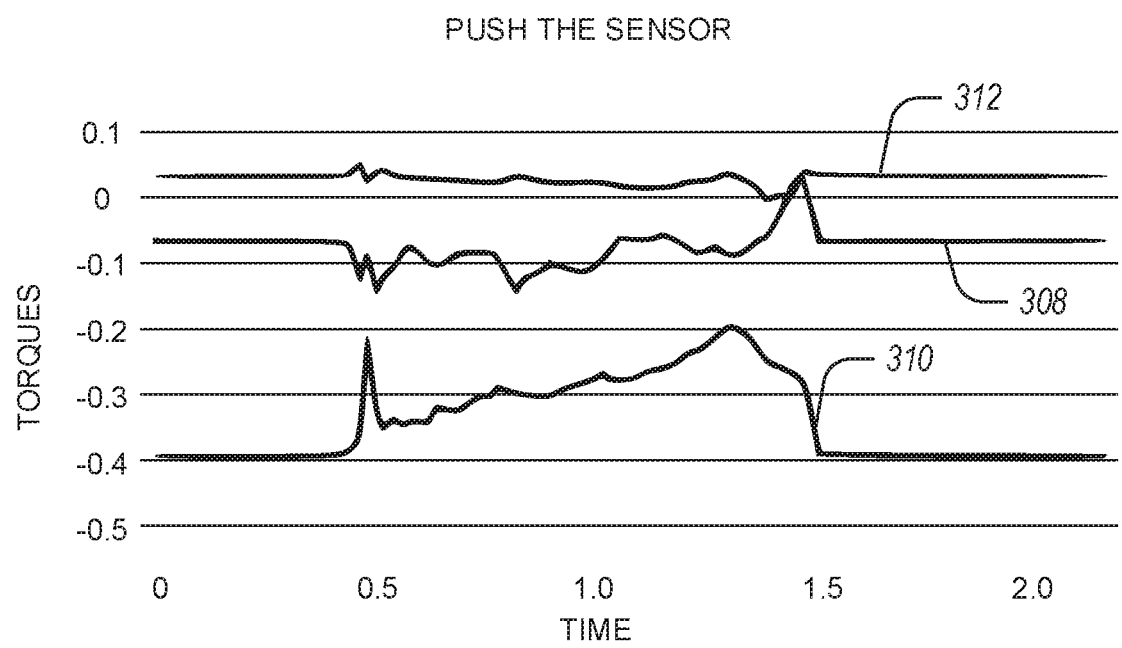
Figure 3E:
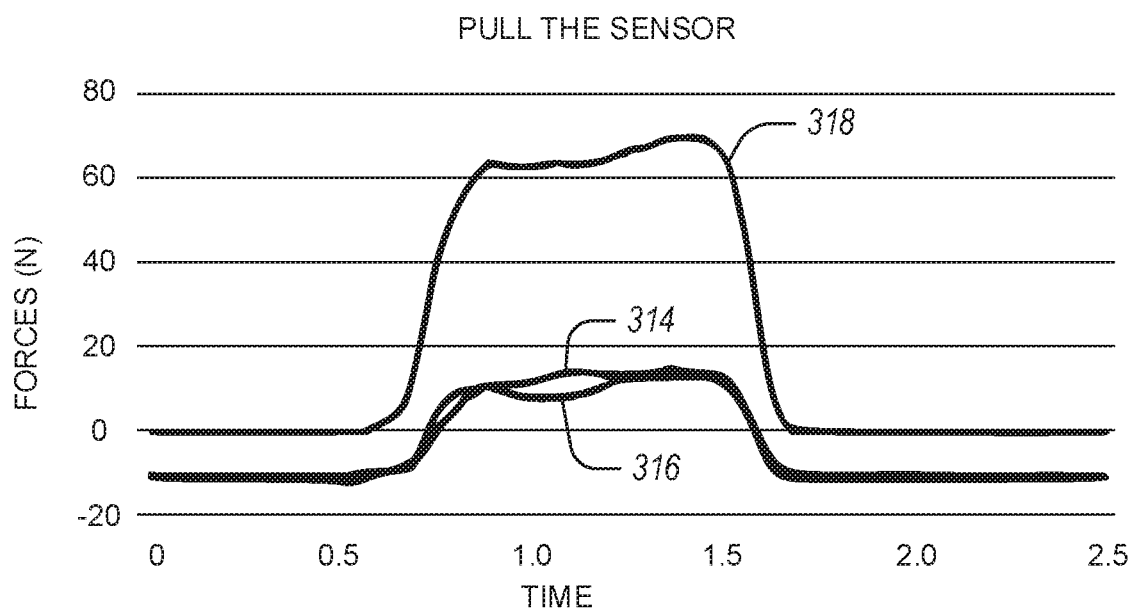
Figure 3F:
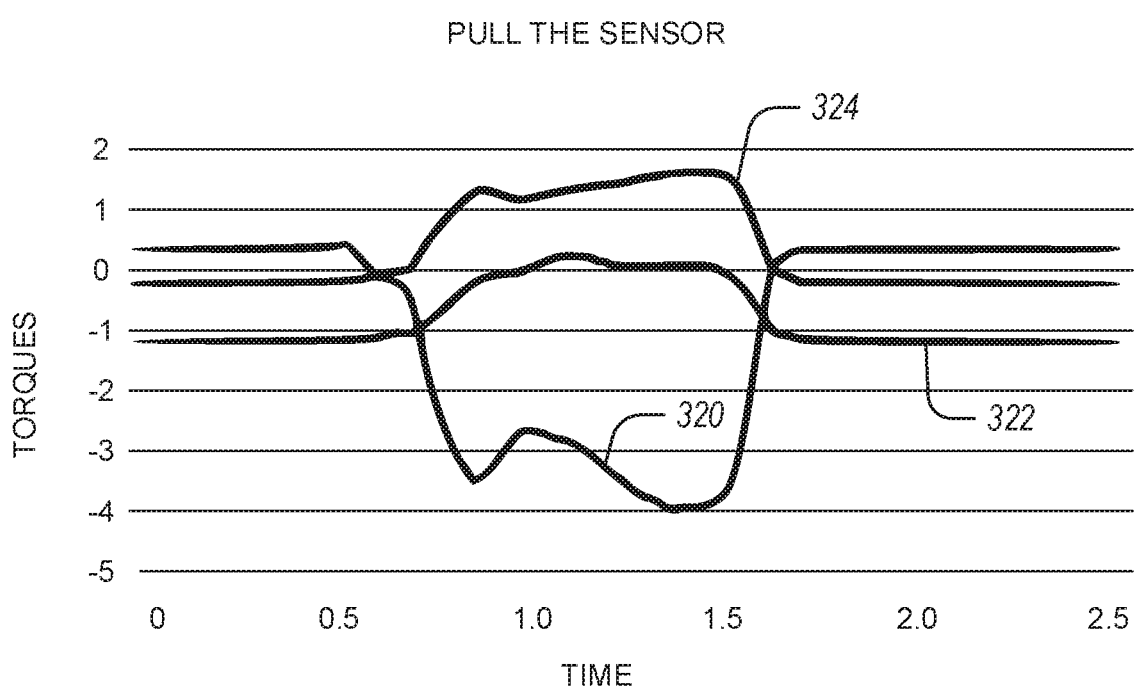

FIGS. 3C-3D show a push applied on a robotic arm in a Z-direction using a force sensor of the robotic arm. FIGS. 3E-3F show a pull applied on a robotic arm in a Z-direction using a force sensor of the robotic arm. In FIG. 3C, force in the x-direction is shown in line 302, force in the y-direction is shown in line 304, and force in the z-direction is shown in line 306. In FIG. 3D, torque in the x-direction is shown in line 308, torque in the y-direction is shown in line 310, and torque in the z-direction is shown in line 312. In FIG. 3E, force in the x-direction is shown in line 314, force in the y-direction is shown in line 316, and force in the z-direction is shown in line 318. In FIG. 3F, torque in the x-direction is shown in line 320, torque in the y-direction is shown in line 322, and torque in the z-direction is shown in line 324. Time is shown in seconds, forces are shown in Newtons, and torque is shown in Newton-meters. Slight variations in force or torque in the x-direction and the y-direction occur for both the push and the pull, however the change in the z-force is significantly higher. A threshold force or torque may be used to determine an intended or likely direction for a push, pull, or tap, for example. The threshold force may be a threshold change in force or torque. The torque stays around zero or negative for the x-direction and y-direction, while the torque is positive in the z-direction (positive and negative may be defined according to a convention, and the opposite signs may be used instead).

Figure 4:
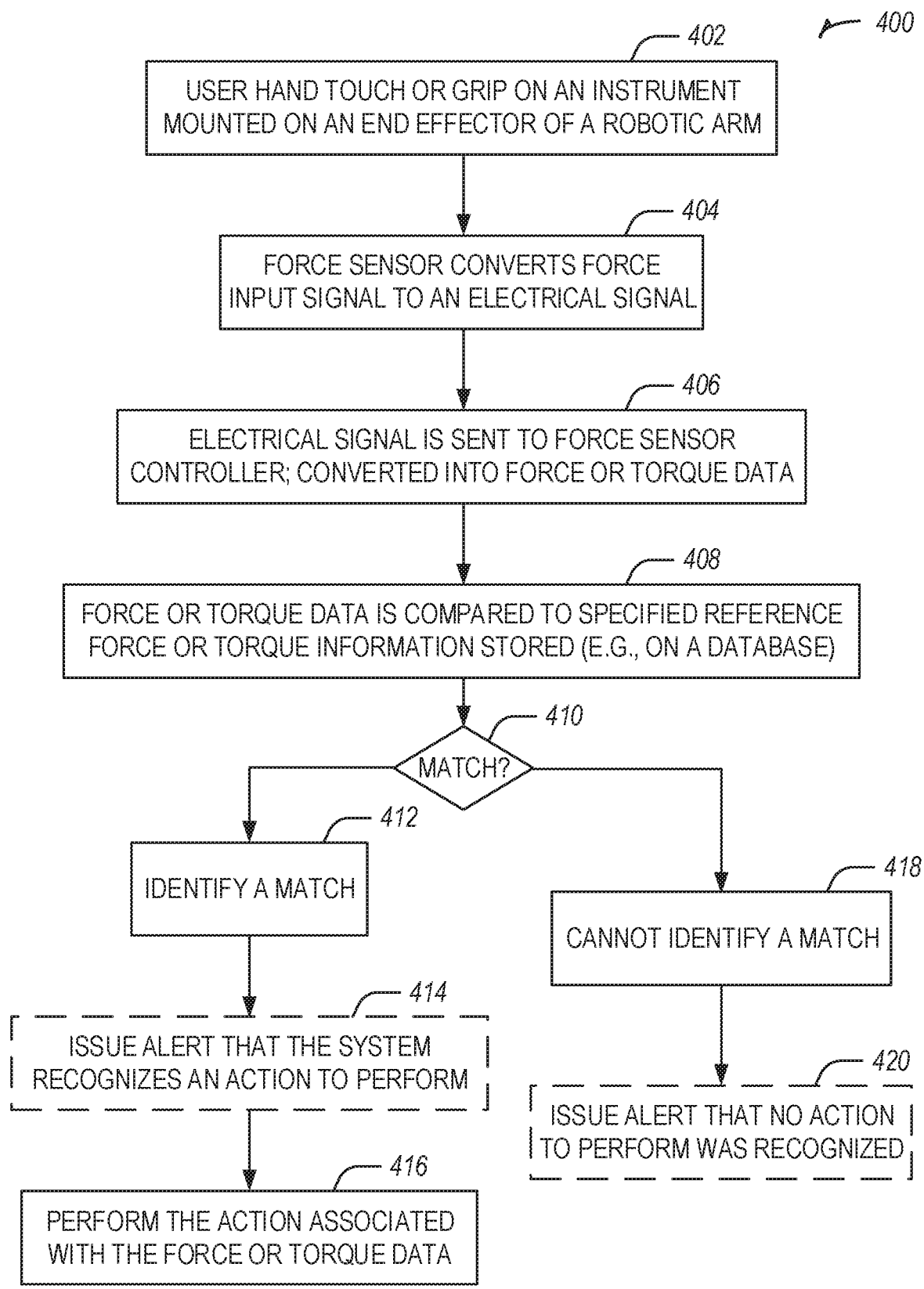
FIGS. 4-5 illustrate flowcharts showing techniques for facilitating interaction between a surgeon and a surgical robot in accordance with at least one example of this disclosure.

FIG. 4 illustrates a flowchart illustrating a technique 400 for facilitating interaction between a surgeon and a surgical robot in accordance with some embodiments.

The technique 400 includes an operation 402 to identify a user hand touch or grip on an instrument mounted on an end effector of a robotic arm.

The technique 400 includes an operation 404 to convert a force input signal to an electrical signal using a force sensor (e.g., on the robotic arm).

The technique 400 includes an operation 406 to send the electrical signal to a force sensor controller (e.g., a processor), which may convert the electrical signal into force or torque data.

The technique 400 includes an operation 408 to compare the force or torque data to specified reference force or torque information stored (e.g., on a database).

The technique 400 includes an operation 410 to determine whether a match is identified.

The technique 400 includes an operation 412 to identify a match.

The technique 400 includes an operation 414 to optionally issue an alert, in response to identifying the match, that the system recognizes an action to perform. In another example, the technique 400 may include issuing an alert when an action is not recognized.

The technique 400 includes an operation 416 to perform the action associated with the force or torque data in response to identifying the match.

The technique 400 includes an operation 418 to fail to identify a match.

The technique 400 includes an operation 420 to issue an alert, in response to identifying the match, that no action to perform was recognized. In another example, the technique 400 may include doing nothing in response to not identifying a match, and optionally return to operation 402.

Figure 5:
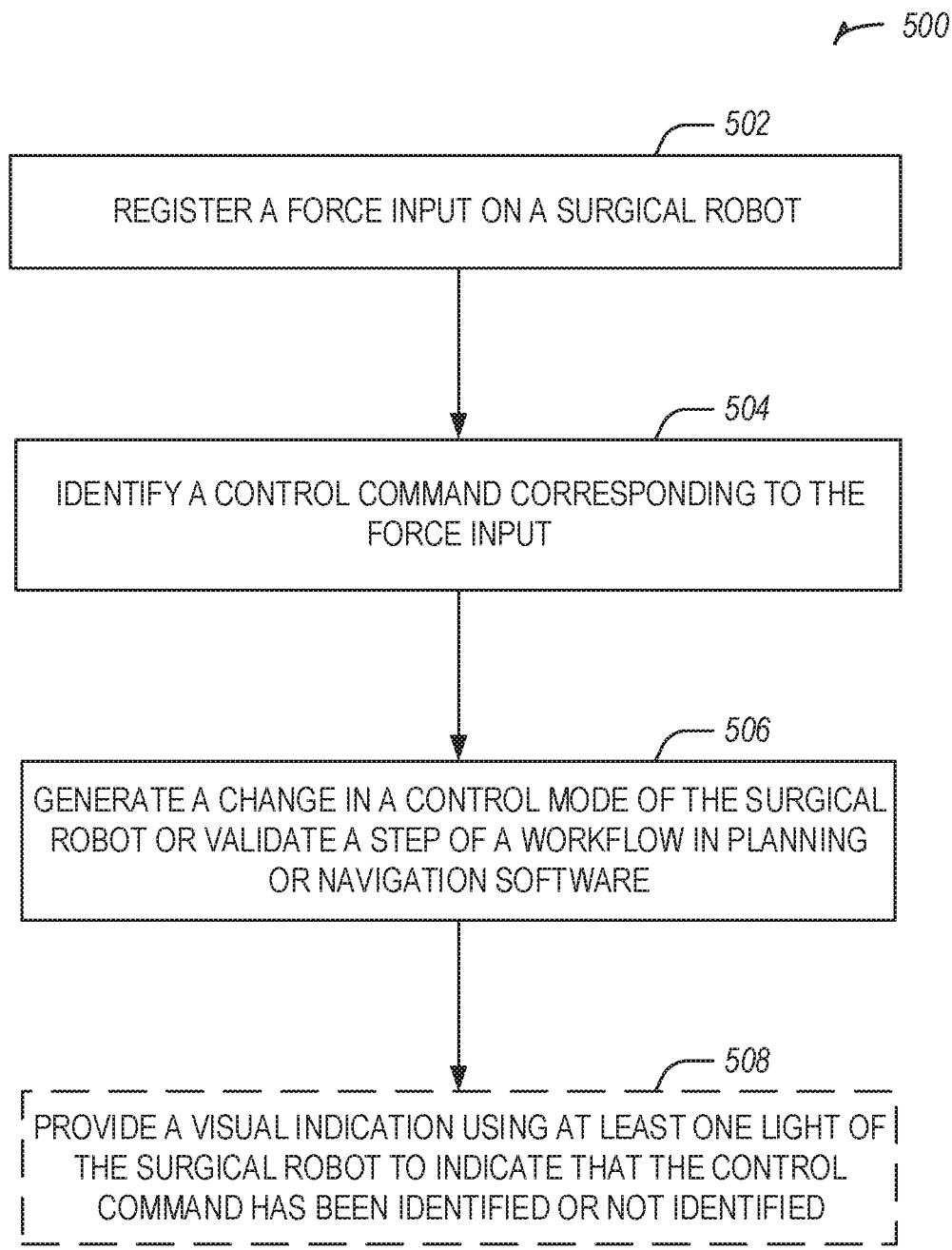

FIG. 5 illustrates a flowchart illustrating a technique 500 for facilitating interaction between a surgeon and a surgical robot in accordance with some embodiments. The technique 500 includes an operation 502 to register a force input on a surgical robot. The force input may include a force applied in a particular direction or amplitude for a specified time.

The technique 500 includes an operation 504 to identify a control command corresponding to the force input. Operation 504 may include determining a match between the force input and the control command stored in a database.

The technique 500 includes an operation 506 to generate a change in a control mode of the surgical robot or validate a step of a workflow in a planned surgery performed using planning or navigation software. In an example, the change in the control mode includes a change from a mode where the force input commands the surgical robot to a mode where the force input controls the planning or navigation software. In an example, operation 506 may be done automatically by a system depending on the surgical workflow steps. When a step requires the use of the planning software, the system may automatically switch to a mode where the force input is used to validate a surgical step of a workflow in planning, for example in navigation software. When a step of the workflow requires the use of the robotic arm (for example when sending the robot end effector to a planned trajectory) the system may automatically switch to the mode where the force input is used for changing the control mode of the robot.

The technique 500 includes an operation 508 to optionally provide a visual indication using at least one light of the surgical robot to indicate that the control command has been identified or not identified. In an example, the visual indication indicates that the control command has been executed. In another example, the visual indication includes flashing the at least one light or changing color of the at least one light. A second visual indication may be used to indicate that the force input was not matched to any control commands.

The technique 500 may include updating a user interface to reflect a next step of the workflow. The technique 500 may include receiving an input indication from a foot pedal or other suitable sensor. In this example, identifying the control command may include using the input indication (e.g., a combination of input indication from different sensors, such as force sensor plus foot pedal, force sensor plus joint motor electric power, foot pedal plus joint motor electric power, etc.). In this example, the control command may be identified as corresponding to the force input only when the foot pedal is depressed. In an example, the surgical robot may be configured to assist in a surgical procedure, the surgical procedure conducted within a field of view of the surgeon. The force input may be received when a distal end of the surgical robot is within the field of view, the force input acting on the distal end of the surgical robot, for example. The technique 500 may include an operation to receive force information corresponding to forces applied by the force input on joints of the robotic arm. In this example, identifying the control command includes using the received force information. Force/torque information may be deduced by using electric power of joint information, which may have different values depending on the force applied on the joint. This function may also be used to detect collisions with the robotic arm and filter the forces imparted on the robotic arm from the collisions.

Figure 6:
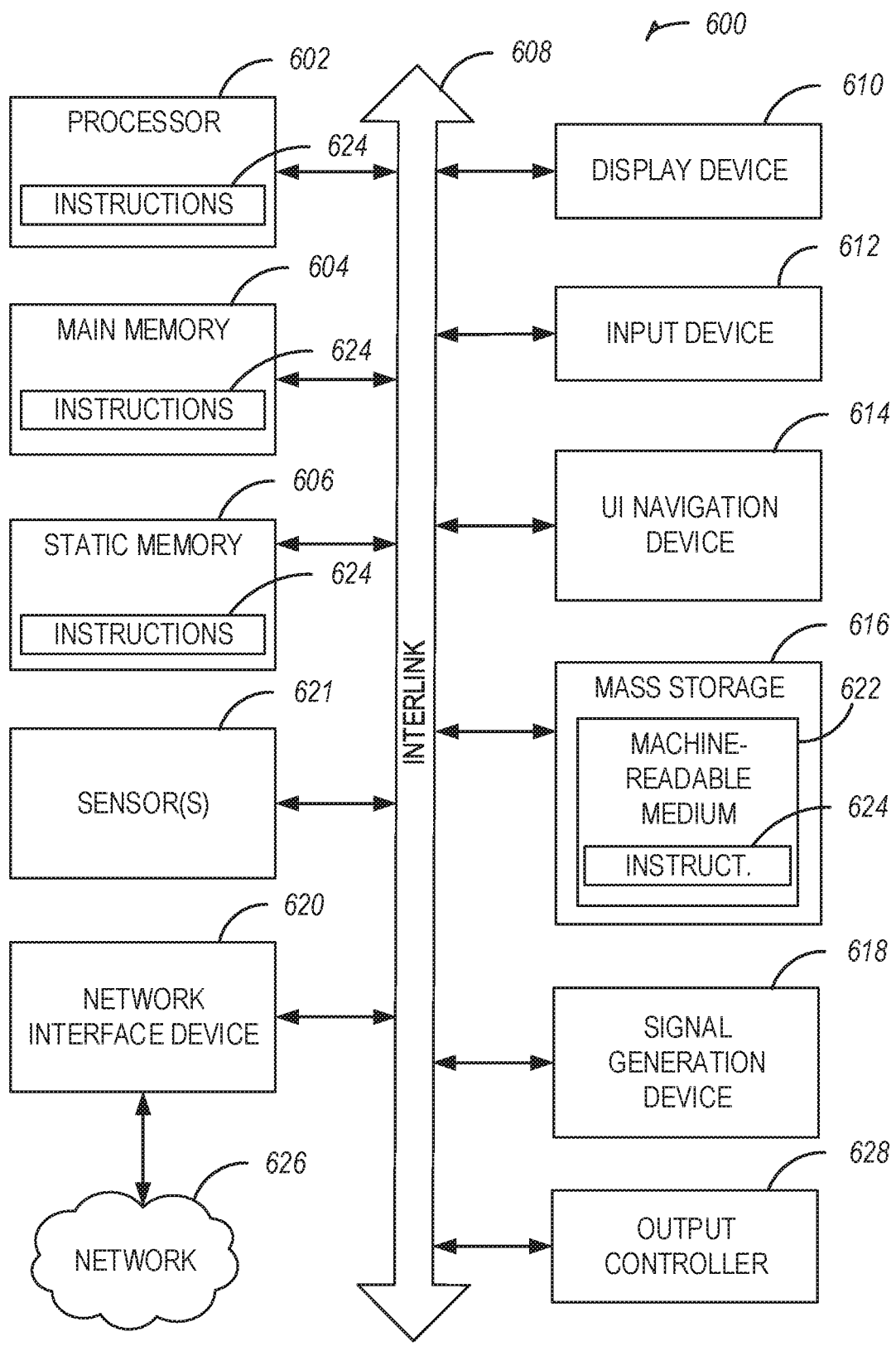
FIG. 6 illustrates a block diagram of an example machine upon which any one or more of the techniques discussed herein may perform in accordance with at least one example of this disclosure.

FIG. 6 illustrates a block diagram of an example machine 600 upon which any one or more of the techniques discussed herein may perform in accordance with some embodiments. In alternative embodiments, the machine 600 may operate as a standalone device or may be connected (e.g., networked) to other machines. In a networked deployment, the machine 600 may operate in the capacity of a server machine, a client machine, or both in server-client network environments. In an example, the machine 600 may act as a peer machine in peer-to-peer (P2P) (or other distributed) network environment. The machine 600 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Machine (e.g., computer system) 600 may include a hardware processor 602 (e.g., a central processing unit (CPU), a graphics processing unit (GPU), a hardware processor core, or any combination thereof), a main memory 604 and a static memory 606, some or all of which may communicate with each other via an interlink (e.g., bus) 608. The machine 600 may further include a display unit 610, an alphanumeric input device 612 (e.g., a keyboard), and a user interface (UI) navigation device 614 (e.g., a mouse). In an example, the display unit 610, input device 612 and UI navigation device 614 may be a touch screen display. The machine 600 may additionally include a storage device (e.g., drive unit) 616, a signal generation device 618 (e.g., a speaker), a network interface device 620, and one or more sensors 621, such as a global positioning system (UPS) sensor, compass, accelerometer, or other sensor. The machine 600 may include an output controller 628, such as a serial (e.g., Universal Serial Bus (USB), parallel, or other wired or wireless (e.g., infrared (IR), near field communication (NFC), etc.) connection to communicate or control one or more peripheral devices (e.g., a printer, card reader, etc.).

The storage device 616 may include a machine readable medium 622 on which is stored one or more sets of data structures or instructions 624 (e.g., software) embodying or utilized by any one or more of the techniques or functions described herein. The instructions 624 may also reside, completely or at least partially, within the main memory 604, within static memory 606, or within the hardware processor 602 during execution thereof by the machine 600. In an example, one or any combination of the hardware processor 602, the main memory 604, the static memory 606, or the storage device 616 may constitute machine readable media.

While the machine readable medium 622 is illustrated as a single medium, the term "machine readable medium" may include a single medium or multiple media (e.g., a centralized or distributed database, and/or associated caches and servers) configured to store the one or more instructions 624. The term "machine readable medium" may include any medium that is capable of storing, encoding, or carrying instructions for execution by the machine 600 and that cause the machine 600 to perform any one or more of the techniques of the present disclosure, or that is capable of storing, encoding or carrying data structures used by or associated with such instructions. Non-limiting machine readable medium examples may include solid-state memories, and optical and magnetic media.

The instructions 624 may further be transmitted or received over a communications network 626 using a transmission medium via the network interface device 620 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 620 may include one or more physical jacks (e.g., Ethernet, coaxial, or phone jacks) or one or more antennas to connect to the communications network 626. In an example, the network interface device 620 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 600, and includes digital or analog communications signals or other intangible medium to facilitate communication of such software.

FIG. 7 illustrates an exploded view of a surgical robotic device 700 in accordance with at least one example of this disclosure. The surgical robotic device 700 may be used with the systems and techniques described herein, for example with techniques 400 and 500 of FIGS. 4 and 5, respectively, and with the surgical robot systems of FIGS. 1A-1E. For example, a force sensor shown in FIG. 7 may be used to control a robotic arm or software component, as described herein.

The surgical robotic device 700 may include components, such as a robotic arm 702, robot end effector 704, a robot or force sensor interface 706, a force sensor 708 (e.g., including a cable connector 710), an electrical insulator 712, a sterile interface 714, or a surgical tool 716 (e.g., a pointer). One or more of these components may be omitted or modified, or other components may be added in some examples. In some examples, components may be arranged to connect to the robotic arm 702 via the robotic end effector 704 proximate the robotic arm 702, for example, in order from proximate to distal, the robot or force sensor interface 706 may connect to the robotic end effector 704, the force sensor 708 connects to the robotic end effector 704, the electrical insulator 712 connects to the force sensor 708, the sterile interface 714 connects to the electrical insulator, and the surgical tool 716 connects to the sterile interface 714.

The surgical robotic device 700 may include detachable or fixed components of the robotic arm. Other system components, such as a computer, a robotic controller, a processor, memory, a camera, lighting, optical navigation components, or the like may be coupled to, in communication with, or otherwise available to the surgical robotic device 700 in some examples.

The surgical robotic device may include a ROSA® robotic device (manufactured by Zimmer CAS of Montreal, Quebec CA), for example the ROSA® Knee System. Other end effectors than the surgical tool shown in FIG. 7 may be used with the surgical robotic device 700. The surgical tool may removable, such as by affixing it (though potentially not directly, as shown in FIG. 7) to the robot end effector. Other tools than strictly surgical tools (e.g., a light) may be used, though surgical tool is used herein for convenience. The tool may be used as an input device to apply a force to the arm portion of the surgical robotic device.

The ROSA® device is a robotized image-guided device that assists the surgeon during surgeries (e.g., brain, spine, knee, etc.). The ROSA® device provides guidance of surgical instruments (drill, saw, needles, etc.) with instrument guides. The ROSA® device allows for a plan of the position of instruments or implants on medical images and provides stable, accurate, and reproducible guidance in accordance with the planning. Adequate guidance of instruments may be obtained from three-dimensional calculations performed from desired surgical planning parameters and registration of spatial position of a patient.

Each of the following non-limiting examples may stand on its own, or may be combined in various permutations or combinations with one or more of the other examples.

Example 1 is a method for facilitating interaction between a surgeon and a surgical robot, the method comprising: registering a force input generated by the surgeon on the surgical robot using a force sensor of the surgical robot; identifying a control command corresponding to the force input; in response to identifying the control command: generating a change in a control mode of the robot; or validating a step of a workflow in planning or navigation software; and providing a visual indication using at least one light of the surgical robot to indicate that the control command has been identified.

In Example 2, the subject matter of Example 1 includes, wherein the visual indication indicates that the control command has been executed.

In Example 3, the subject matter of Examples 1-2 includes, wherein identifying the control command includes determining a match between the force input and the control command stored in a database.

In Example 4, the subject matter of Examples 1-3 includes, updating a user interface to reflect a next step of the workflow.

In Example 5, the subject matter of Examples 1-4 includes, wherein the change in the control mode includes a change from a mode where the force input commands the surgical robot to a mode where the force input controls the planning or navigation software.

In Example 6, the subject matter of Examples 1-5 includes, receiving an input indication from a foot pedal, and wherein identifying the control command includes using the input indication.

In Example 7, the subject matter of Example 6 includes, wherein the control command is identified as corresponding to the force input only when the foot pedal is depressed.

In Example 8, the subject matter of Examples 1-7 includes, wherein the visual indication includes flashing the at least one light or changing color of the at least one light, and wherein a second visual indication is used to indicate that the force input was not matched to any control commands.

In Example 9, the subject matter of Examples 1-8 includes, wherein the surgical robot is configured to assist in a surgical procedure, the surgical procedure conducted within a field of view of the surgeon, and wherein the force input is received when a distal end of the surgical robot is within the field of view, the force input acting on the distal end of the surgical robot.

In Example 10, the subject matter of Examples 1-9 includes, wherein the force input includes a force applied in a particular direction for a specified time.

In Example 11, the subject matter of Examples 1-10 includes, receiving force information corresponding to forces applied by the force input on joints of the robotic arm, and wherein identifying the control command includes using the received force information.

Example 12 is at least one machine-readable medium including instructions for facilitating interaction between a surgeon and a surgical robot, which when executed by a processor, cause the processor to: register a force input generated by the surgeon on the surgical robot using a force sensor of the surgical robot; identify a control command corresponding to the force input; in response to identifying the control command: generate a change in a control mode of the robot; or validate a step of a workflow in planning or navigation software; and provide a visual indication using at least one light of the surgical robot to indicate that the control command has been identified.

In Example 13, the subject matter of Example 12 includes, wherein the visual indication indicates that the control command has been executed.

In Example 14, the subject matter of Examples 12-13 includes, wherein the instructions to identify the control command include instructions to determine a match the force input and the control command stored in a database.

In Example 15, the subject matter of Examples 12-14 includes, wherein the instructions further include instructions to update a user interface to reflect a next step of the workflow.

In Example 16, the subject matter of Examples 12-15 includes, wherein the change in the control mode includes a change from a mode where the force input commands the surgical robot to a mode where the force input controls the planning or navigation software.

In Example 17, the subject matter of Examples 12-16 includes, wherein the instructions further include instructions to receive an input indication from a foot pedal, and wherein the instructions to identify the control command include instructions to use the input indication.

In Example 18, the subject matter of Example 17 includes, wherein the control command is identified as corresponding to the force input only when the foot pedal is depressed.

In Example 19, the subject matter of Examples 12-18 includes, wherein the visual indication includes a flashing of the at least one light or a changing of color of the at least one light, and wherein a second visual indication is used to indicate that the force input was not matched to any control commands.

In Example 20, the subject matter of Examples 12-19 includes, wherein the surgical robot is configured to assist in a surgical procedure, the surgical procedure conducted within a field of view of the surgeon, and wherein the force input is received when a distal end of the surgical robot is within the field of view, the force input acting on the distal end of the surgical robot.

In Example 21, the subject matter of Examples 12-20 includes, wherein the force input includes a force applied in a particular direction for a specified time.

In Example 22, the subject matter of Examples 12-21 includes, wherein the instructions further include instructions to receive force information corresponding to forces applied by the force input on joints of the robotic arm, and wherein the instructions to identify the control command include instructions to use the received force information.

Example 23 is a system comprising: a surgical robot comprising: a force sensor to register a force input generated by a surgeon on the surgical robot; and at least one light; and a processor, communicatively coupled to the surgical robot, the processor configured to: identify a control command corresponding to the force input; and in response to identifying the control command: generate a change in a control mode of the robot; or validate a step of a workflow in planning or navigation software; and provide an indication that the control command has been identified by outputting a command to cause the at least one light to provide a visual indication.

In Example 24, the subject matter of Example 23 includes, wherein the visual indication indicates that the control command has been executed.

In Example 25, the subject matter of Examples 23-24 includes, wherein to identify the control command, the processor is further configured to determine a match between the force input and the control command stored in a database.

In Example 26, the subject matter of Examples 23-25 includes, wherein the processor is further configured to output an update to a user interface to reflect a next step of the workflow.

In Example 27, the subject matter of Examples 23-26 includes, wherein the change in the control mode includes a change from a mode where the force input commands the surgical robot to a mode where the force input controls the planning or navigation software.

In Example 28, the subject matter of Examples 23-27 includes, wherein the processor is further configured to receive an input indication from a foot pedal, and wherein to identify the control command, the processor is further configured to use the input indication.

In Example 29, the subject matter of Example 28 includes, wherein the control command is identified as corresponding to the force input only when the foot pedal is depressed.

In Example 30, the subject matter of Examples 23-29 includes, wherein the visual indication includes a flashing of the at least one light or a changing of color of the at least one light, and wherein a second visual indication is used to indicate that the force input was not matched to any control commands.

In Example 31, the subject matter of Examples 23-30 includes, wherein the surgical robot is configured to assist in a surgical procedure, the surgical procedure conducted within a field of view of the surgeon, and wherein the force input is received when a distal end of the surgical robot is within the field of view, the force input acting on the distal end of the surgical robot.

In Example 32, the subject matter of Examples 23-31 includes, wherein the force input includes a force applied in a particular direction for a specified time.

In Example 33, the subject matter of Examples 23-32 includes, wherein the processor is further configured to receive force information corresponding to forces applied by the force input on joints of the robotic arm, and wherein to identify the control command, the processor is further configured to use the received force information.

In Example 34, the subject matter of Examples 23-33 includes, wherein the processor includes a robotic controller component.

In Example 35, the subject matter of Examples 1-34 is performed during a hip arthroplasty surgery.

Example 36 is a system comprising: a surgical robot comprising: a force sensor of a robotic arm to register a force input generated by a surgeon on the surgical robot; and a processor, communicatively coupled to the surgical robot, the processor configured to: receive a gesture (e.g., a double tap) on the robotic arm toggle a speed of the robotic arm.

In Example 37, the subject matter of Example 36 includes, wherein the speed of the robotic arm is changed from a first speed in free movement to a second, slower speed when the robotic arm is in proximity of a connector to an instrument to facilitate a connection with the instrument (i.e. docking).

Example 38 is at least one machine-readable medium including instructions that, when executed by processing circuitry, cause the processing circuitry to perform operations to implement of any of Examples 1-37.

Example 39 is an apparatus comprising means to implement of any of Examples 1-37.

Example 40 is a system to implement of any of Examples 1-37.

Example 41 is a method to implement of any of Examples 1-37.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

What is claimed is:
1. A system comprising:
 a surgical robot comprising:
  a force sensor to register a force input generated by a surgeon on the surgical robot; and
  at least one light; and
 a processor, communicatively coupled to the surgical robot, the processor configured to:
  identify a control command corresponding to the force input; and
  in response to identifying the control command:
   validate a step of a workflow in planning or navigation software;
   in response to validating the step, change to a next step in the planning or navigation software and output a control signal to cause the surgical robot to change to a next planned trajectory based on validating the step of the workflow; and
   provide an indication that the control command has been identified by outputting a command to cause the at least one light to provide a visual indication.

2. The system of claim 1, wherein the visual indication indicates that the control command has been executed.

3. The system of claim 1, wherein to identify the control command, the processor is further configured to determine a match between the force input and the control command stored in a database.

4. The system of claim 1, wherein the processor is further configured to output an update to a user interface to reflect a next step of the workflow.

5. The system of claim 1, wherein the processor is further configured to receive an input indication from a foot pedal, and wherein to identify the control command, the processor is further configured to use the input indication.

6. The system of claim 5, wherein the control command is identified as corresponding to the force input only when the foot pedal is depressed.

7. The system of claim 1, wherein the visual indication includes a flashing of the at least one light or a changing of color of the at least one light, and wherein a second visual indication is used to indicate that the force input was not matched to any control commands.

8. The system of claim 1, wherein the surgical robot is configured to assist in a surgical procedure, the surgical procedure conducted within a field of view of the surgeon, and wherein the force input is received when a distal end of the surgical robot is within the field of view, the force input acting on the distal end of the surgical robot.

9. The system of claim 1, wherein the force input includes a force applied in a particular direction for a specified time.

10. The system of claim 1, wherein the processor is further configured to receive force information corresponding to forces applied by the force input on joints of the surgical robot, and wherein to identify the control command, the processor is further configured to use the received force information.

11. A method for facilitating interaction between a surgeon and a surgical robot, the method comprising:
registering a force input generated by the surgeon on the surgical robot using a force sensor of the surgical robot, the force sensor affixed to an end effector of the surgical robot;
identifying a control command corresponding to the force input;
in response to identifying the control command:
validating a step of a workflow in planning or navigation software;
in response to validating the step, changing to a next step in the planning or navigation software and outputting a control signal to cause the surgical robot to change to a next planned trajectory based on validating the step of the workflow; and
providing a visual indication using at least one light of the surgical robot to indicate that the control command has been identified.

12. The method of claim 11, wherein the visual indication indicates that the control command has been executed.

13. The method of claim 11, wherein identifying the control command includes determining a match between the force input and the control command stored in a database.

14. The method of claim 11, further comprising updating a user interface to reflect a next step of the workflow.

15. The method of claim 11, further comprising receiving an input indication from a foot pedal, and wherein identifying the control command includes using the input indication.

16. The method of claim 11, wherein the surgical robot is configured to assist in a surgical procedure, the surgical procedure conducted within a field of view of the surgeon, and wherein the force input is received when a distal end of the surgical robot is within the field of view, the force input acting on the distal end of the surgical robot.

17. The method of claim 11, further comprising receiving force information corresponding to forces applied by the force input on joints of the surgical robot, and wherein identifying the control command includes using the received force information.

18. At least one machine-readable medium including instructions for facilitating interaction between a surgeon and a surgical robot, which when executed by a processor, cause the processor to:
register a force input generated by the surgeon on the surgical robot using a force sensor of the surgical robot;
identify a control command corresponding to the force input;
in response to identifying the control command:
validate a step of a workflow in planning or navigation software;
in response to validating the step, change to a next step in the planning or navigation software and output a control signal to cause the surgical robot to change to a next planned trajectory based on validating the step of the workflow; and
provide a visual indication using at least one light of the surgical robot to indicate that the control command has been identified.

* * * * *